US009506878B2

(12) United States Patent
Teshima (10) Patent No.: US 9,506,878 B2
(45) Date of Patent: Nov. 29, 2016

(54) STRUCTURAL BODY AND X-RAY TALBOT INTERFEROMETER INCLUDING THE STRUCTURAL BODY

(71) Applicant: CANON KABUSHIKI KAISHA, Tokyo (JP)

(72) Inventor: Takayuki Teshima, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 170 days.

(21) Appl. No.: 14/553,865

(22) Filed: Nov. 25, 2014

(65) Prior Publication Data

US 2015/0151527 A1 Jun. 4, 2015

(30) Foreign Application Priority Data

Nov. 29, 2013 (JP) ................. 2013-247127

(51) Int. Cl.
*G03H 5/00* (2006.01)
*G01N 23/20* (2006.01)
(Continued)

(52) U.S. Cl.
CPC ....... *G01N 23/20075* (2013.01); *A61B 6/4035* (2013.01); *A61B 6/484* (2013.01); *B32B 1/00* (2013.01); *B32B 3/30* (2013.01); *B32B 7/12* (2013.01); *B32B 15/08* (2013.01); *B32B 27/306* (2013.01); *B32B 37/1284* (2013.01); *B32B 38/1866* (2013.01); *G21K 1/067* (2013.01); *G21K 1/10* (2013.01); *B32B 38/10* (2013.01); *B32B 2037/1253* (2013.01); *B32B 2037/243* (2013.01); *B32B 2307/728* (2013.01); *B32B 2307/73* (2013.01); *B32B 2309/105* (2013.01); *B32B 2311/04* (2013.01); *B32B 2457/00* (2013.01); *B32B 2551/00* (2013.01); *C25D 1/04* (2013.01); *C25D 1/08* (2013.01); *C25D 7/123* (2013.01); *G21K 2201/067* (2013.01); *G21K2207/005* (2013.01); *Y10T 156/10* (2015.01); *Y10T 428/24331* (2015.01); *Y10T 428/24545* (2015.01)

(58) Field of Classification Search
CPC ............... G03H 5/00; G21K 2207/00; G21K 2207/005; G21K 2201/061; G21K 2201/064; G21K 2201/067; G21K 1/067; A61B 6/484; A61B 6/4035; G01N 23/20075
USPC ......................................... 378/36
See application file for complete search history.

(56) References Cited

U.S. PATENT DOCUMENTS 4,704,325 A 11/1987 Crocker
6,540,844 B1 4/2003 Crook
(Continued)

FOREIGN PATENT DOCUMENTS

CN 1423263 A 6/2003
CN 101425456 A 5/2009
(Continued)

OTHER PUBLICATIONS

Yueping et al, Developments of X-Ray Grating Imaging Based on Talbot Interferometry, Lasers and Optoelectronics Progress, pp. 9-16 (2012).

*Primary Examiner* — Jurie Yun
(74) *Attorney, Agent, or Firm* — Canon U.S.A. Inc., IP Division (57) ABSTRACT

A structural body, comprising: a resin layer with a curved surface; a first bonding layer containing a water-soluble polymer; a second bonding layer having a hydrogen-bonding surface; and a gold layer in this order, the first bonding layer being between, and in contact with, the curved surface of the resin layer and the hydrogen-bonding surface of the second bonding layer.

20 Claims, 6 Drawing Sheets

(51) Int. Cl.
*A61B 6/00* (2006.01)
*G21K 1/06* (2006.01)
*G21K 1/10* (2006.01)
*B32B 7/12* (2006.01)
*B32B 15/08* (2006.01)
*B32B 27/30* (2006.01)
*B32B 1/00* (2006.01)
*B32B 3/30* (2006.01)
*B32B 37/12* (2006.01)
*B32B 38/18* (2006.01)
*B32B 37/24* (2006.01)
*C25D 7/12* (2006.01)
*C25D 1/04* (2006.01)
*C25D 1/08* (2006.01)
*B32B 38/10* (2006.01)

(56) References Cited

U.S. PATENT DOCUMENTS

| | | |
|---|---|---|
| 2005/0046943 A1 | 3/2005 | Suganuma |
| 2006/0113279 A1 | 6/2006 | Little |
| 2007/0183583 A1 | 8/2007 | Baumann et al. |
| 2009/0110144 A1 | 4/2009 | Takahashi |
| 2009/0214838 A1 | 8/2009 | Lussem et al. |
| 2010/0246769 A1 | 9/2010 | David et al. |
| 2012/0140883 A1 | 6/2012 | Iwakiri |

FOREIGN PATENT DOCUMENTS

| | | |
|---|---|---|
| CN | 102472847 A | 5/2012 |
| JP | sho61-197236 A | 9/1986 |
| JP | 2007-206075 A | 8/2007 |
| JP | 2011-047015 A | 3/2011 |

STRUCTURAL BODY AND X-RAY TALBOT INTERFEROMETER INCLUDING THE STRUCTURAL BODY

BACKGROUND OF THE INVENTION

1. Field of the Invention

The present invention relates to a structural body and an X-ray Talbot interferometer that includes the structural body.

2. Description of the Related Art

Diffractive gratings that include a structural body having a periodic structure are used as optical elements in various apparatuses. In particular, X-ray optical elements containing gold, which has high X-ray absorptivity, are used in non-destructive inspection of substances using X-rays and in the medical field.

An application of X-ray optical elements containing gold is the shield grating of Talbot interferometers, the latter of which acquire information on a subject utilizing X-ray Talbot interference.

X-ray Talbot interferometry will be briefly described below. X-ray Talbot interferometry is one of a number of imaging methods (X-ray phase imaging methods) utilizing X-ray phase contrast.

In general X-ray Talbot interferometers, a spatially coherent X-ray is diffracted by a diffractive grating and forms an interference pattern. A moiré pattern is formed by placing a shield grating configured periodically to block an X-ray at a position where the interference pattern is formed. The moiré pattern is detected with a detector. A subject disposed between an X-ray source and the shield grating changes the moiré pattern. Information (in general, phase image information, differential phase contrast image information, scattering image information, or absorption image information) on the subject can be obtained from this change in the moiré pattern.

General shield gratings for use in Talbot interferometry have a structure in which X-ray transmission portions (hereinafter also referred to simply as transmission portions) and X-ray shield portions (hereinafter also referred to simply as shield portions) are periodically arranged. The X-ray shield portion is often composed of gold, which has high X-ray absorptivity. Even using a highly-absorbent material such as gold in a shield portion, the shield portion structure has a high aspect ratio based on the relationship between the thickness required for X-ray shielding and the period of the interference pattern impinging on the shield grating (the aspect ratio is the ratio (h/w) of the height or depth h to the width w of the shield portion). Hereinbelow, a shield grating composed of gold is considered to be a type of gold layer. Flat shield gratings are useful when parallel light (e.g. a parallel X-ray) is used, for example, in synchrotron radiation facilities. However, like laboratory X-ray tubes, in the case of imaging using spherical waves emitted by an X-ray source, which is a point light source for emitting divergent light (a divergent X-ray), the X-ray propagation direction deviates from the height direction of the shield portion with increasing distance from the optical axis (the X-ray axis). This also blocks an X-ray that should be transmitted through the shield grating, resulting in an insufficient X-ray transmission contrast or a low X-ray dosage that reaches a detector. These may result in increased noise in the information on the subject or no information on the subject in a peripheral region that is distant from the optical axis.

Japanese Patent Laid-Open No. 2007-206075 (US counterpart: 2007/0183583) discloses a method for conforming the height direction of the shield portion to the X-ray propagation direction by placing a shield grating in a vacuum chamber and two-dimensionally bending the shield grating by the action of a differential pressure, thereby bending the shield grating along a spherical surface to match the wavefront of the divergent X-ray.

In order to retain the curved shape of the shield grating using the method according to Japanese Patent Laid-Open No. 2007-206075, however, the differential pressure must be continuously applied to the shield grating. Thus, it may be difficult to retain the curved shape of the shield grating. Gold layers other than gratings suffer the same problems.

SUMMARY OF THE INVENTION

The present invention provides a structural body, comprising:
a resin layer with a curved surface;
a first bonding layer containing a water-soluble polymer;
a second bonding layer having a hydrogen-bonding surface; and
a gold layer in this order,
the first bonding layer being between, and in contact with, the curved surface of the resin layer and the hydrogen-bonding surface of the second bonding layer.

Other aspects of the present invention will be described below in the description of the embodiments.

Further features of the present invention will become apparent from the following description of example of executions with reference to the attached drawings.

DESCRIPTION OF THE EMBODIMENTS

Embodiments of the present invention will be described in detail below.

A structural body that can easily retain the curved shape of a gold layer and an X-ray Talbot interferometer that includes the structural body are described in the following embodiments. The structural body includes a gold layer having a curved shape and can be used as a bent shield grating in the same manner as the shield grating described in Japanese Patent Laid-Open No. 2007-206075.

A structural body according to the present embodiment includes a resin layer (resin sheet), a first bonding layer, a second bonding layer, and a gold layer in this order. The resin layer has a curved surface. The curved surface is in contact with the first bonding layer. The first bonding layer is in contact with a hydrogen-bonding surface of the second bonding layer. A first surface of the first bonding layer is in contact with the curved surface of the resin layer. Since the structural body includes the resin layer, the first bonding layer, the second bonding layer, and the gold layer in this order, a second surface of the first bonding layer opposite the first surface is in contact with the hydrogen-bonding surface of the second bonding layer. The second bonding layer includes at least one layer, and at least one surface of the second bonding layer is the hydrogen-bonding surface. The gold layer is bonded to the second bonding layer. Any and all the layers between the gold layer and the first bonding layer are considered to be the second bonding layer.

Thus, the gold layer is bonded to the curved surface of the resin layer with the second bonding layer and the first bonding layer interposed therebetween and therefore has a curved shape. The gold layer may have an uneven thickness and may have holes (through-holes) or recess portions (closed-end holes). A gold layer composed of a gold X-ray shield grating functions as a bent X-ray shield grating.

The embodiments of the present invention will be described below with reference to the drawings.

A structural body 1 will be described below with reference to FIGS. 1A to 1F. FIGS. 1A to 1F are cross-sectional views of the structural body 1. In the structural body 1 illustrated in FIG. 1, a curved surface 4 of a resin layer 5 is bonded to a gold layer 2 with a first bonding layer 6 and a second bonding layer 3 interposed therebetween. Thus, the gold layer 2 has a curved shape along the curved surface 4 of the resin layer 5. Each of the layers will be described below.

The resin layer 5 has the curved surface 4. Although the resin layer 5 has the curved surface 4 in contact with the first bonding layer 6, the other surface of the resin layer 5 may be a flat surface or a curved surface. The curved surface 4 may have any shape. A spherical (including a spherical crown), aspheric, or cylindrical curved surface 4 can provide a spherically, aspherically, or cylindrically bent gold layer 2, respectively. The gold layer 2 can be bent into the desired shape by determining the shape and size of the curved surface 4 while taking account of the thickness of the second bonding layer 3 and the thickness of the first bonding layer 6. In the case where a gold layer is used as a shield grating of a Talbot interferometer that utilizes a divergent X-ray, since the difference between the propagation direction of the divergent X-ray and the height direction of the gold layer should be minimized, the curved surface 4 can be such that the gold layer 2 is bent along the wavefront of the divergent X-ray. The curved surface that allows the gold layer 2 to be bent along the wavefront of a two-dimensional divergent X-ray (for example, a cone beam) is a spherical surface. The curved surface that allows the gold layer 2 to be bent along the wavefront of a one-dimensional divergent X-ray (for example, a fan beam) is a cylindrical surface.

Examples of the resin that forms the resin layer 5, include, but are not limited to, acrylic resins, epoxy resins, and polycarbonate resins. When the gold layer 2 is used as an X-ray shield grating of a Talbot interferometer, the resin layer 5 can be formed of an acrylic resin. This is because acrylic resins are used as optical lens materials, and precision processing technology for optical lens processing can be utilized in the manufacture of the resin layer 5.

The first bonding layer 6 is a bonding layer between the curved surface 4 of the resin layer 5 and the second bonding layer 3 and contains a water-soluble polymer. The first bonding layer 6 has a first surface (the bottom in FIG. 1A) and a second surface 10 (the top surface in FIG. 1A). The first surface is in contact with the curved surface 4 of the resin layer 5. The first surface of the first bonding layer 6 is not shown in FIGS. 1A to 1F because it does not need to be discriminated from the curved surface 4 for the purpose of description. The second surface 10 is opposite the first surface and is in contact with a hydrogen-bonding surface 11 of the second bonding layer 3.

The water-soluble polymer of the first bonding layer 6 can be selected from surfactants that are solid at normal temperature. In the case where the environment during the use of the structural body 1 is not at normal temperature, a surfactant that is solid in the environment is selected. In the case where the structural body 1 is used at normal temperature, the water-soluble polymer for use in the present embodiment can be a nonionic surfactant, such as polyvinyl alcohol, polyethylene glycol, or a polyoxyethylene alkyl ether. Among these, polyvinyl alcohol after solidification can be firmly bonded to the hydrogen-bonding surface and is relatively poorly soluble in water at normal temperature. The first bonding layer 6 can be formed of a water-soluble polymer and may contain a plurality of water-soluble polymers. The first bonding layer 6 may contain a water-insoluble polymer. In the case where the first bonding layer 6 contains a water-insoluble polymer, the water-insoluble polymer can have a particle diameter of between 1 μm and 3 μm inclusive, and the water-insoluble polymer content of the first bonding layer 6 can be 3% or less.

The water-soluble polymer(s) of the first bonding layer 6 can be used to bond the curved surface 4 of the resin layer 5 and the gold layer 2 together without causing damage to the curved surface 4. When a water-insoluble, fat-soluble bonding agent dissolved in an organic solvent (for example, a bonding agent containing an organic solvent) is used to bond the gold layer 2 and the curved surface 4 of the resin layer 5 together, the curved surface 4 often dissolves in the organic solvent and has an undesired shape. Thus, using a water-soluble polymer reduces this risk and is preferred.

The curved surface 4 of the resin layer 5 is bonded to the hydrogen-bonding surface of the second bonding layer 3 via the first bonding layer 6. Thus, even when the second bonding layer 3 and the gold layer 2 bonded to the second bonding layer 3 are bonded to the curved surface 4 while they are elastically deformed, the gold layer 2 can easily follow the curved shape of the resin layer 5 and is firmly bonded to the resin layer 5. Even when the second bonding layer 3 and the gold layer 2 are elastically deformed, this results in higher adaptability to the curved shape than the case where only the periphery of the gold layer 2 is bonded to the curved surface 4 of the resin layer 5. When the second bonding layer 3 and the gold layer 2 are bonded to the curved surface 4 so as to follow the shape of the curved surface 4 of the resin layer 5, the shape of the gold layer 2 reflects the shape of the curved surface 4 of the resin layer 5. Thus, the curved shape of the gold layer 2 is similar to the curved shape of the resin layer 5.

The second bonding layer 3 has at least one hydrogen-bonding surface 11. The surface of gold is resistant to oxidation and nitriding. Thus, the surface of the gold layer 2 is a hydrophobic surface rather than a hydrogen-bonding surface. Even when the gold layer 2 and the curved surface 4 of the resin layer 5 are bonded together using a bonding method that utilizes hydrogen bonding, therefore, it is not necessarily easy to maintain reliable bonding. Thus, it is difficult to bond the resin layer 5 and the gold layer 2 together using a water-soluble bonding agent. Furthermore, as described above, bonding the resin layer 5 and the gold layer 2 together using a fat-soluble bonding agent dissolved in an organic solvent may result in dissolution of the resin layer 5. In the present embodiment, the gold layer 2 and the first bonding layer 6 are bonded together via the second bonding layer 3 having the hydrogen-bonding surface. Thus, the curved surface 4 of the resin layer 5 and the gold layer 2 can be bonded together utilizing hydrogen bonding. The gold layer 2 and the second bonding layer 3 can be bonded together using any bonding method. For example, at least the surface of the second bonding layer 3 in contact with the gold layer 2 may be formed of a metal other than gold, and the gold layer 2 and the second bonding layer 3 may be bonded together by metal bonding. Alternatively, the second bonding layer 3 and the gold layer 2 may be bonded together by forming an alloy layer at the interface therebetween. Alternatively, the gold layer 2 and at least the surface of the second bonding layer 3 in contact with the gold layer 2 may be formed of a material that is resistant to an organic solvent, and the gold layer 2 and the second bonding layer 3 may be bonded together using a fat-soluble bonding agent.

The second bonding layer 3 is not necessarily a monolayer and may be a multilayer. For example, the second bonding layer 3 may be composed of two layers: a chromium or titanium layer that can adhere securely to the gold layer 2 and a layer formed of a hydrogen-bonding material. Although the second bonding layer 3 has holes corresponding to the holes in the gold layer 2 in FIG. 1A, the second bonding layer 3 may have no holes corresponding to the holes in the gold layer 2.

The term "hydrogen bonding", as used herein, refers to bonding formed by the action of electrostatic attraction between a hydrogen atom covalently bonded to an electronegative atom, for example, in a hydroxy group (—OH) or an amino group (—NH) and an unshared electron pair of another functional group. The hydrogen-bonding surface 11 may be formed of any metal oxide, metal nitride, metalloid oxide, or metalloid nitride, provided that the surface 11 has a hydrogen-bonding property. Examples of the metal oxide include, but are not limited to, copper, iron, nickel, tin, silver, titanium, chromium, and aluminum oxides. The metal oxides, as used herein, include alloy oxides. Examples of the alloy oxides include oxides of alloys of gold and copper, iron, nickel, tin, silver, titanium, chromium, and aluminum. Oxides of copper, iron, nickel, tin, silver, titanium, chromium, and aluminum alloys may also be used. Examples of the metal nitride include, but are not limited to, copper, iron, nickel, tin, silver, titanium, chromium, and aluminum nitrides. The metal nitrides, as used herein, include alloy nitrides. Examples of the alloy nitrides include copper, iron, nickel, tin, silver, titanium, chromium, and aluminum alloy nitrides.

Examples of the metalloid oxide include, but are not limited to, silicon and germanium oxides. Examples of the metalloid nitride include, but are not limited to, silicon, boron, titanium, and chromium nitrides.

Variations in the total thickness of the first bonding layer 6 and the second bonding layer 3 can be 8% or less of the maximum thickness of the gold layer 2. This is because a large variation in thickness results in a deviation from the design curved shape of the gold layer 2 even when the shape of the curved surface 4 is adjusted to the curved shape of the gold layer 2.

The gold layer 2 is formed of gold and contains 99% or more gold. The gold layer 2 in FIG. 1A has a plurality of holes 7. The holes 7 are not necessarily empty spaces. A material other than gold, such as silicon or a resin, may be disposed in the holes 7. Silicon or a resin in the holes 7 can strengthen the holes 7. The holes 7 in the present embodiment may have any shape and may be cylindrical, cylindroid, or polygonal columnar (including holes having a linear cross section perpendicular to the height direction). Although the gold layer 2 in FIG. 1A appears to be divided by the holes 7, the gold layer 2 in FIG. 1A has a mesh structure, and portions of the gold layer 2 between the holes 7 are linked to each other.

Figure 1A:
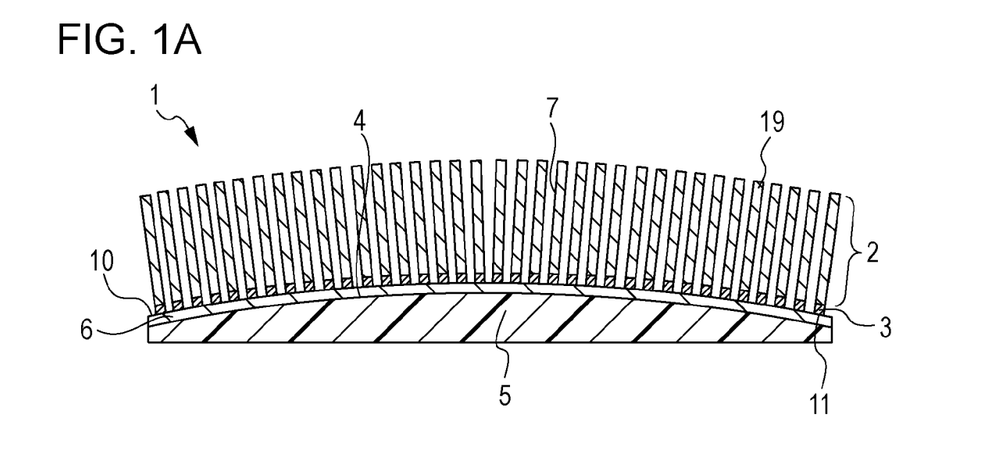
FIGS. 1A to 1F are schematic cross-sectional views of a structural body according to embodiments of the present invention.
Figure 1B:
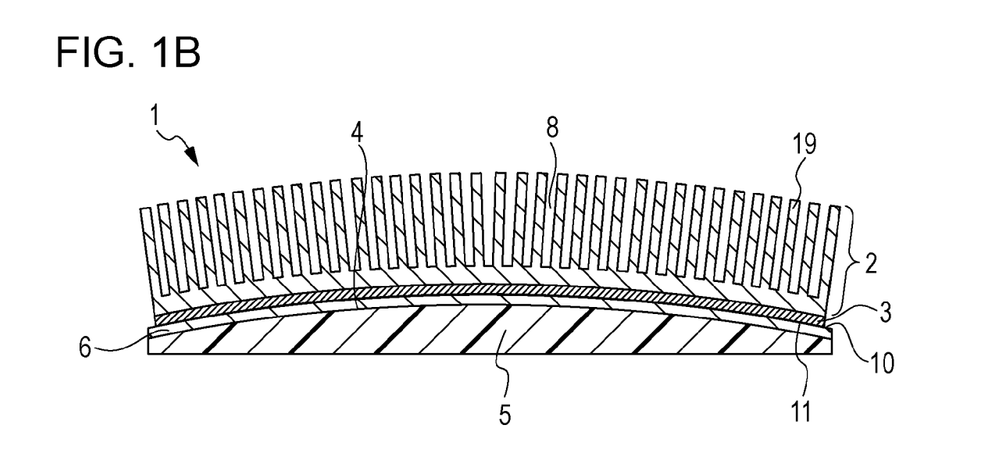

As illustrated in FIG. 1B, the gold layer 2 according to the present embodiment may have a plurality of recess portions 8. The recess portions 8 are not necessarily empty spaces and may be filled with a material other than gold, such as silicon or a resin. The recess portions 8 in the present embodiment may have any shape and may be cylindrical, cylindroid, or polygonal columnar (including recess portions having a linear cross section perpendicular to the height direction).

Figure 1C:
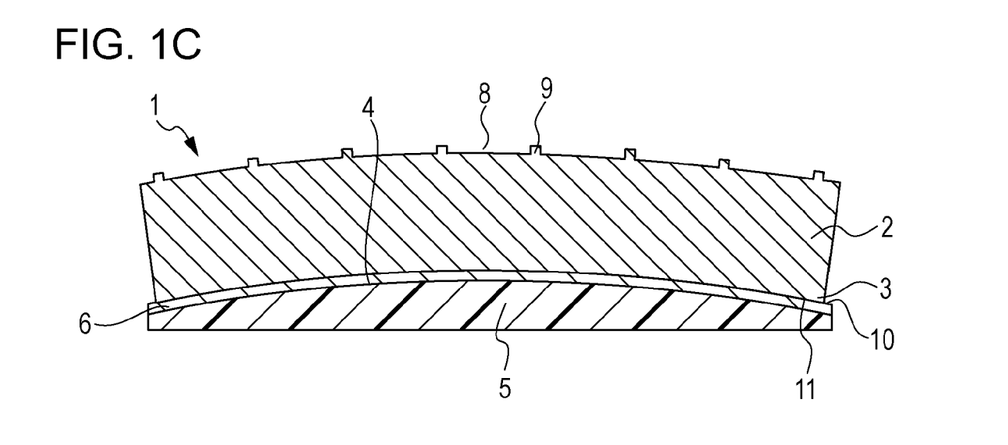

As illustrated in FIG. 1C, the recess portions 8 of the gold layer 2 may have a depth smaller than the thickness of the gold layer 2 or may have a width greater than half the interval between the recess portions 8. In the case where the recess portions 8 have a width greater than half the interval between the recess portions 8, the gold layer 2 in FIG. 1C appears to be a gold layer having a uniform thickness on which a plurality of protrusions 9 are disposed.

Although not shown in the figures, the gold layer 2 may have a uniform thickness. Although the gold layer 2 cannot be used as an X-ray shield grating in this case, the present invention can be widely applied to other applications that use a gold layer having a curved shape.

The gold layer 2 of the structural body 1 according to the present embodiment can be used as a shield grating configured to block part of a divergent X-ray. In this case, the gold layer 2 can have a plurality of holes 7 (FIG. 1A). In the case where the gold layer 2 of the structural body 1 in FIG. 1A is used as an X-ray shield grating, a gold region 19 of the gold layer 2 functions as a shield portion, and the holes 7 function as transmission portions. The resin layer 5, the first bonding layer 6, and the second bonding layer 3 function as supporting members for supporting the shield grating (the gold layer 2). X-rays pass relatively unaffected through the resin layer 5, and the first and second bonding layers 6 and 3.

Figure 2:
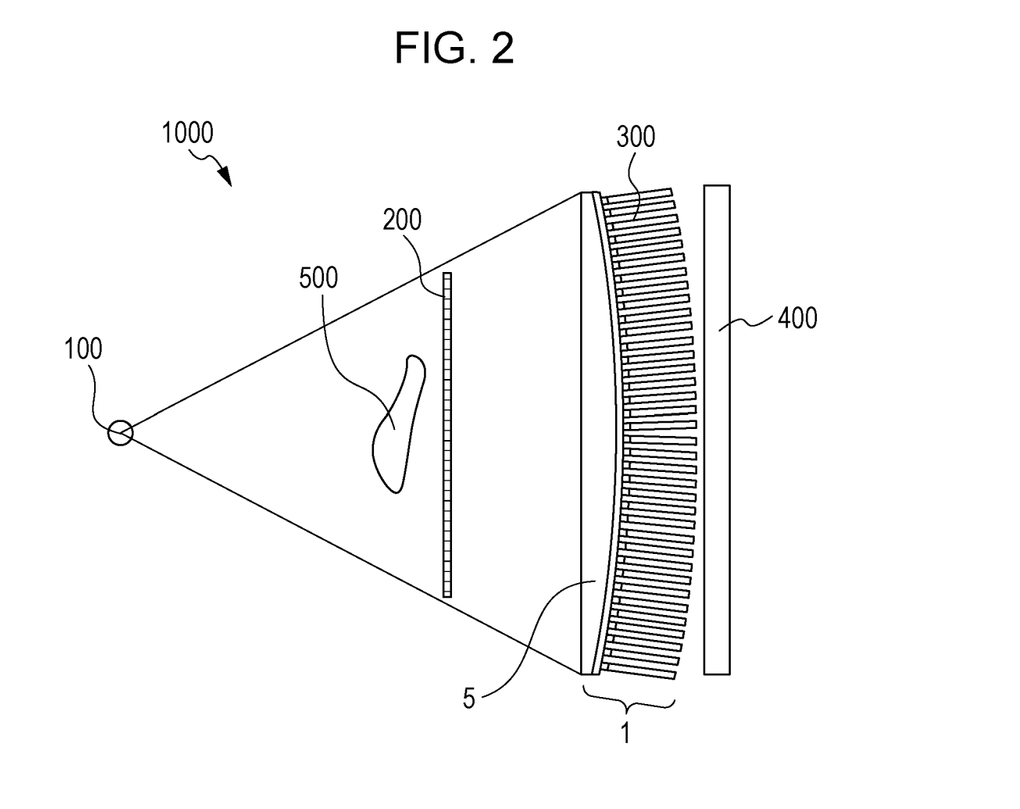
FIG. 2 is a schematic view of a Talbot interferometer that includes a structural body according to an embodiment or example of execution of the present invention.

The shield grating may be used in an X-ray Talbot interferometer, as illustrated in FIG. 2. The gold layer 2 in the flat state includes a plurality of holes 7 in the vertical direction. When the gold layer 2 is bonded to the curved surface 4, the holes 7 are arranged in the direction perpendicular to the curved surface 4 of the resin layer 5. The structural body 1 includes the bent gold layer 2 having a radius of curvature that corresponds to the distance from an X-ray source 100. This structure can decrease a difference between the X-ray propagation direction and the height direction of the X-ray shield portion with increasing distance from the optical axis in measurements (image pickup) using an X-ray source as a point light source. This is effective in facilitating X-ray transmission and increasing the X-ray transmission contrast. Furthermore, since the resin layer 5 that maintains the shape of the gold layer 2 is formed of a resin that transmits X-rays, there is little risk of X-ray transmission loss. In the case where the gold layer 2 having the holes 7 is used as a shield grating of a Talbot interferometer, the holes 7 have an aspect ratio of between 7 and 60 inclusive. The intervals between the holes 7 (the intervals between the centers thereof) can be between 0.5 μm and 10 μm inclusive. In the case where the gold layer 2 includes the recess portions 8 (FIG. 1B), the recess portions 8 can have an aspect ratio of between 7 and 60 inclusive. The intervals between the recess portions 8 can be between 0.5 μm and 10 μm inclusive.

Although not shown in FIG. 2, a source grating may be disposed between the X-ray source 100 and a diffractive grating 200 (in the case where a subject 500 is disposed between the X-ray source 100 and the diffractive grating, the source grating may be disposed between the X-ray source 100 and the subject 500). Even when the divergent X-ray from the X-ray source 100 has low coherence, a source grating can be used to form a virtual arrangement of minute X-ray sources and form an interference pattern through a diffractive grating. In particular, Talbot interferometry using a source grating is referred to as Talbot-Lau interferometry. The gold layer 2 of the structural body 1 according to the present embodiment can also be used as a source grating. In Talbot interferometry, it is known that no shield grating is required when an interference pattern can be directly detected. In a Talbot-Lau interferometer without a shield grating, the gold layer 2 of the structural body 1 according to the present embodiment can also be used as a source grating. The structural body 1 according to the present embodiment can also be used as an optical element other than shield gratings.

The present invention will be described in detail below, purely by way of example, with specific example of executions.

Example of Execution 1

The structural body 1 illustrated in FIG. 1A is described in the present example of execution. The structural body 1 includes the gold layer 2 having a plurality of holes 7 arranged in two crossing directions (i.e. in two dimensions). A method for forming the gold layer 2 and the second bonding layer 3 according to the present example of execution will be described below with reference to FIGS. 3A to 3E.

Figure 3A:
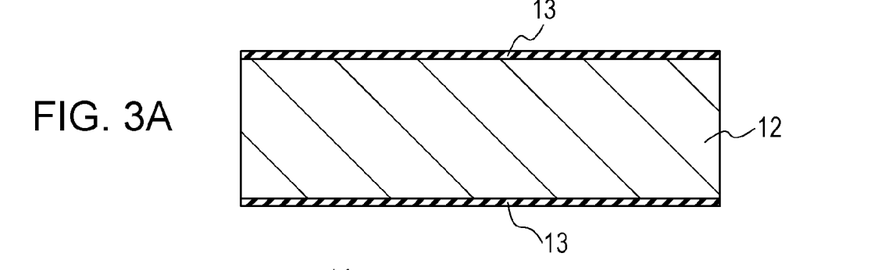
FIGS. 3A to 3E are explanatory views of a method for manufacturing a structural body according to an example of execution of the present invention.

A silicon substrate 12 having a diameter of 100 mm, a thickness of 525 μm, and a resistivity of 0.02 Ωcm is used as a substrate. A thermal oxide film 13 having a thickness of approximately 0.5 μm is formed on the front and back sides of the silicon substrate 12 by thermally oxidizing the silicon substrate 12 at 1050° C. for 75 minutes (FIG. 3A).

Figure 3B:
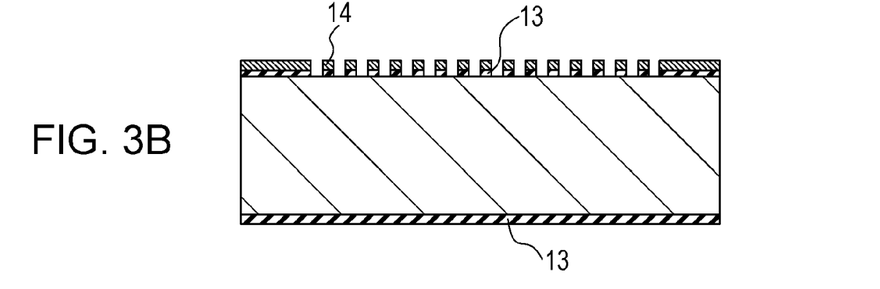

A chromium mask 14 having a thickness of 200 nm is formed on one side of the silicon substrate 12 with an electron beam vapor deposition apparatus. A positive resist is applied to the chromium mask 14. Photoresist dot patterns each having a diameter of 4 μm are two-dimensionally formed at intervals of 8 μm in a 55 mm×55 mm region on the positive resist by semiconductor photolithography. The chromium not coated with the photoresist is then etched with an aqueous chromium etchant. Subsequently, the thermal oxide film 13 is etched by reactive etching using $CHF_3$. Thus, chromium dot patterns each having a diameter of 4 μm are two-dimensionally formed at intervals of 8 μm in the 55 mm×55 mm silicon bare surface (FIG. 3B). In the present example of execution, the chromium mask 14 is used as an etching mask.

Figure 3C:
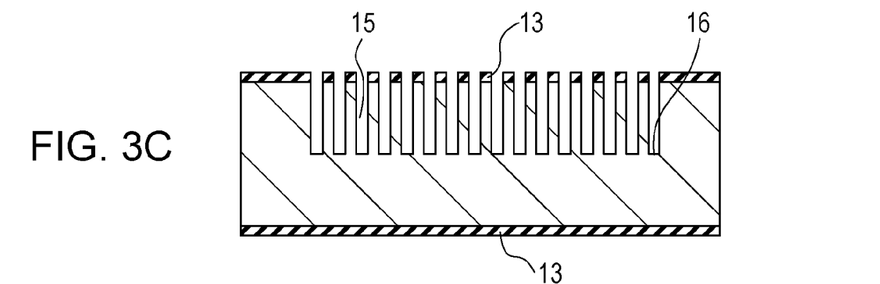

Subsequently, exposed silicon after inductively coupled plasma-reactive ion etching (ICP-RIE) is subjected to anisotropic deep etching. The deep etching is stopped at a depth of approximately 120 μm. Thus, a plurality of recesses (or recess portions) 15 having a depth of approximately 120 μm are formed in the silicon substrate 12 (FIG. 3C).

Subsequently, the photoresist and chromium are removed by UV ozone asking and using the aqueous chromium etchant. The silicon substrate 12 is washed with a liquid mixture of sulfuric acid and a hydrogen peroxide solution and then with water, and is dried.

A thermal oxide film 13 having a thickness of approximately 0.1 μm is then formed by thermal oxidation at 1050° C. for 7 minutes on the surface of the silicon substrate 12 on which the recess portions 15 have been formed. The thermal oxide film 13 on the bottom face 16 of the recess portions 15 is removed using a $CHF_3$ plasma dry etching method. This etching has high anisotropy and proceeds substantially perpendicularly to the silicon substrate 12. Thus, after the thermal oxide film 13 on the bottom face 16 of the recess portions 15 in the silicon substrate 12 is removed, the thermal oxide film 13 remains on the side wall of the recess portions 15.

A chromium film having a thickness of approximately 7.5 nm and a copper film having a thickness of approximately 50 nm are then formed in this order with an electron beam vapor deposition apparatus, thereby forming a seed electrode layer formed of chromium and copper on the silicon bare surface on the bottom face 16 of the recess portions 15. The vapor deposition method with the electron beam vapor deposition apparatus has high directionality and forms a film on the bottom face 16 of the recess portions 15 and on the top face of the silicon substrate 12 between the recess portions 15.

Figure 3D:
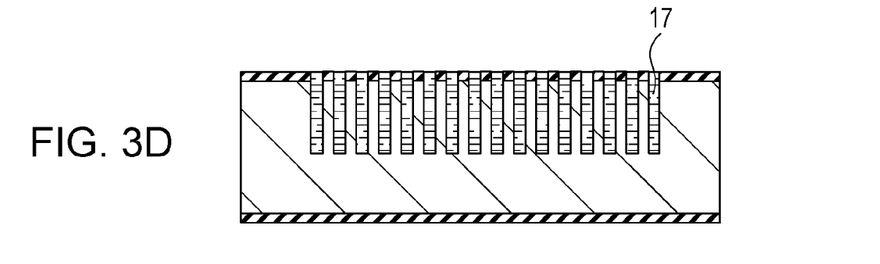

Part of the thermal oxide film 13 formed in a region of the silicon substrate 12 in which no pattern is formed is then removed to expose the silicon surface, which is used as an electroplating lead electrode. The recess portions 15 are filled with a metal by electroplating using the lead electrode as a mold. In the present example of execution, the metal is gold. The gold plating solution is Microfab Au1101 (manufacturer: Electroplating Engineers of Japan Ltd.). A gold plated layer 17 having a height of approximately 120 μm is formed by electroplating. The gold plated layer 17 corresponds to the gold layer 2 of the structural body 1. The silicon substrate 12 is immersed in the gold plating solution and is energized using the lead electrode of the exposed silicon surface as a negative electrode at 60° C. and at a current density of 0.2 A/dm$^2$ for 26 hours, thus forming the gold plated layer 17 until the gold plated layer 17 overflows from the recess portions 15. The overflowed gold plated layer is removed by chemical mechanical polishing (CMP) (FIG. 3D). The gold in the recess portions 15 and copper on the surface of the seed electrode layer are heated to an electroplating temperature of 60° C. and form an alloy at the interface therebetween.

Figure 3E:
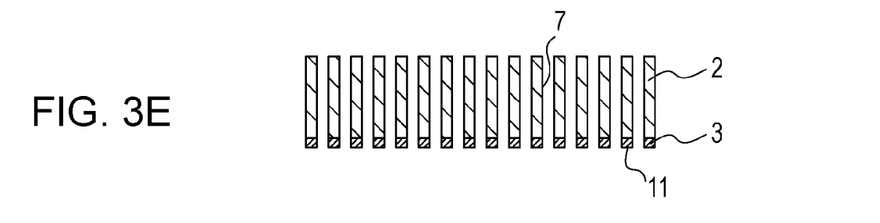

The silicon substrate 12 and the thermal oxide film 13 are etched (i.e. removed) using 30% aqueous potassium hydroxide at 100° C., thus forming the gold layer 2 on its own having a plurality of holes 7 and having a size of 55 mm×55 mm. The gold and copper on the surface of the seed electrode layer are heated to an etching temperature of 100° C. and form an alloy at the interface therebetween. The gold layer 2 formed using this method in the flat state includes a plurality of holes 7 in the vertical direction (in the thickness direction of the gold layer 2 and the height direction of the holes 7). The holes 7 are two-dimensionally arranged at intervals of 8 μm. The holes 7 have empty space. The gold layer 2 is then immersed in an aqueous solution of ceric ammonium nitrate and perchloric acid. Although chromium and copper in the seed electrode layer are removed by etching, the gold-copper alloy layer remains. After washing with water, the gold layer 2 is dried, and the surface of the gold-copper alloy layer is oxidized and forms an oxide film. The alloy layer corresponds to the second bonding layer 3, and the oxide film of the alloy layer corresponds to the hydrogen-bonding surface 11 (FIG. 3E). The alloy layer (the second bonding layer 3) is bonded to the gold layer 2 by electroplating.

In the present example of execution, the gold-copper alloy layer is used as the second bonding layer 3. The surface of the gold layer 2 opposite the surface (also referred to as a contact surface between the gold layer 2 and the second bonding layer 3) on which the alloy layer is formed has no alloy layer and is a gold surface.

In the present example of execution, the resin layer 5 having the curved surface 4 is formed of an acrylic resin. The resin layer 5 includes a convex structural body in a region having a diameter of 80 mm. The radius of curvature of the convex structural body is 1196.8 mm. 5% aqueous polyvinyl alcohol is applied to the curved surface 4. The second bonding layer 3 bonded to the gold layer 2 is placed on the curved surface 4 (with the gold layer 2 facing outwards) such that the hydrogen-bonding surface 11 comes into contact with the aqueous polyvinyl alcohol applied to the curved surface 4 (that is, the hydrogen-bonding surface 11 is disposed on the curved surface 4 with the aqueous polyvinyl alcohol interposed therebetween). Alternatively, the aqueous polyvinyl alcohol may be applied to the hydrogen-bonding surface 11 of the second bonding layer 3 or both the curved surface 4 and the hydrogen-bonding surface 11. The surface of the gold layer 2 opposite the surface in contact with the second bonding layer 3 is then pressurized using a rubber balloon filled with air. This pressurization allows excess aqueous polyvinyl alcohol between the second bonding layer 3 and the curved surface 4 to seep through the holes (empty spaces), and the gold layer 2 to conform to the curved surface 4. As a result of the drying of the aqueous polyvinyl alcohol, the gold layer 2 is firmly bonded to the curved surface 4 of the resin layer 5 with the second bonding layer 3 and the first bonding layer 6 interposed therebetween. Thus, the empty spaces in the second bonding layer 3 and the gold layer 2 allow excess aqueous polymer solution between the second bonding layer 3 and the curved surface 4 to seep through the holes, thereby decreasing variations in the thickness of the first bonding layer 6. Instead of the empty spaces in the second bonding layer 3 and the gold layer 2, recess portions in the second bonding layer 3 can also contain the excess aqueous polymer solution and produce the same effect. The depth of the recess portions may be smaller than the thickness of the second bonding layer 3 (that is, the recess portions are within the second bonding layer 3) or greater than the thickness of the second bonding layer 3 (that is, the recess portions are also disposed in the gold layer 2). Such recess portions in the second bonding layer 3 increase the contact area between the second bonding layer 3 and the first bonding layer 6 and improve adhesion therebetween. For example, when the radius of curvature of the convex structural body is 2000 mm or less, the intervals between the holes or the recess portions on the hydrogen-bonding surface 11 of the second bonding layer 3 is preferably 20 μm or less, more preferably 10 μm or less, because this allows excess aqueous polymer solution between the second bonding layer 3 and the curved surface 4 to seep through the holes or the recess portions and thereby significantly decrease (or eliminate) variations in the thickness of the first bonding layer 6. In the case where the width of the recess portions is greater than the intervals between the recess portions, the recess portions may not contain all of the excess polymer. Thus, the width of the recess portions can be less than ⅔rds of the width of the intervals between the recess portions. In the case where the holes have a shallow depth, excess aqueous polymer solution seeps from the surface of the gold layer 2 opposite the surface in contact with the second bonding layer 3. Thus, the total thickness of the second bonding layer 3 and the gold layer 2 can be 50 μm or more. A material, such as silicon or a resin, can be disposed in the holes after the second bonding layer 3 is bonded to the curved surface 4 via the first bonding layer 6.

In the case where the external shape of the curved surface 4 of the resin layer 5 is greater than the external shape of the gold layer 2 as in the present example of execution, excess aqueous polymer solution between the second bonding layer 3 and the curved surface 4 is efficiently discharged along the curved surface 4. This can decrease variations in the thickness of the first bonding layer 6.

Figure 1D:
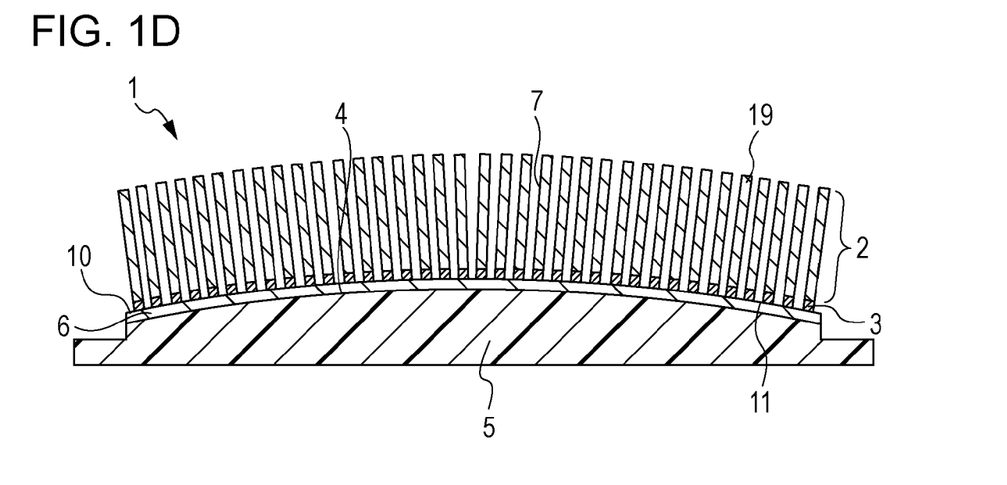
Figure 1E:
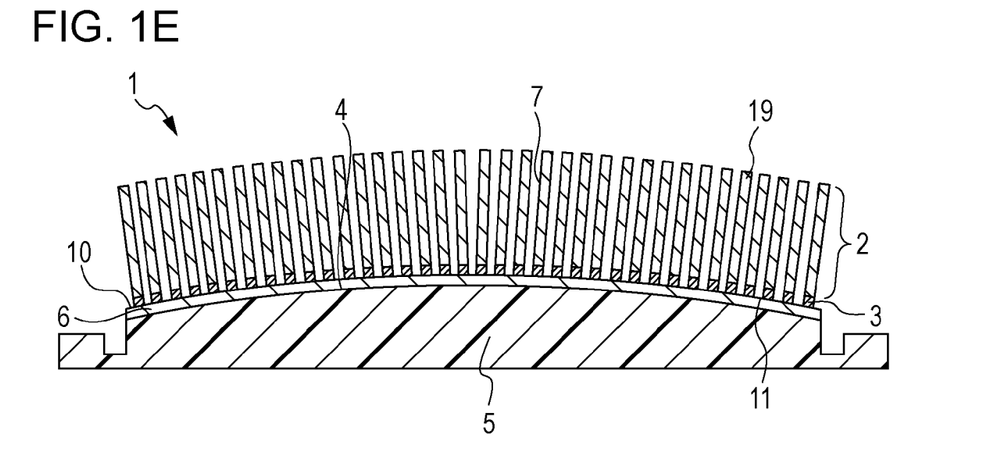
Figure 4:
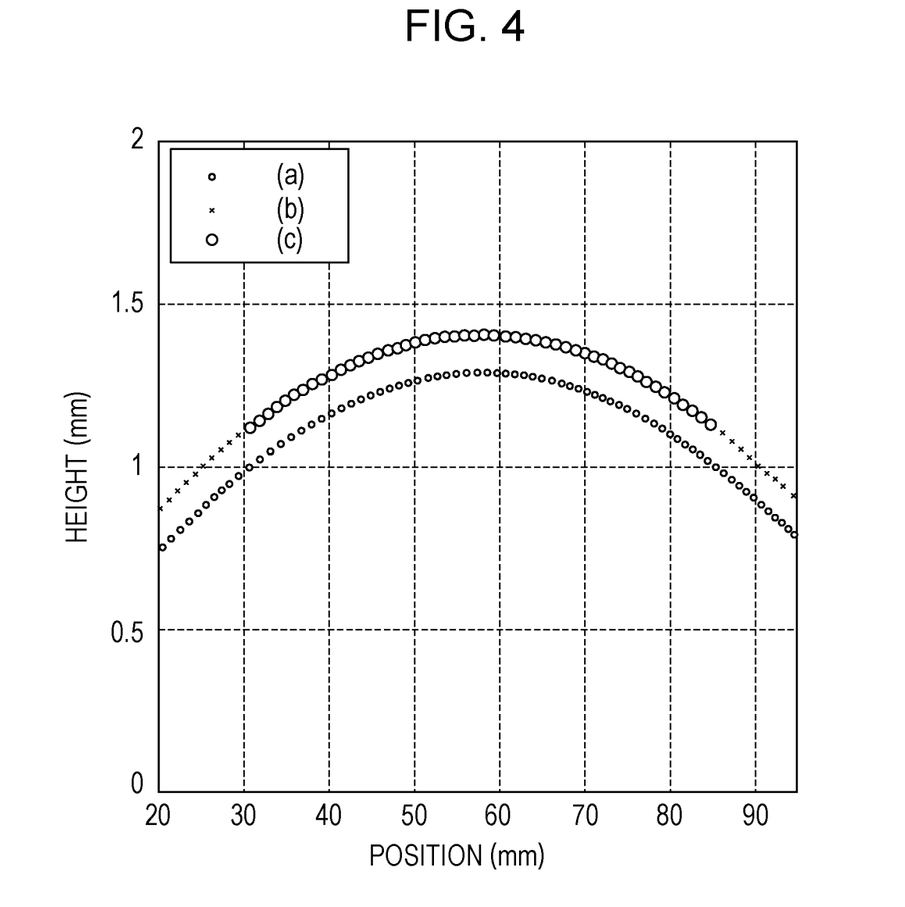
FIG. 4 is a graph for explaining an embodiment of the present invention.

Formation of a groove in the periphery of the curved surface 4 of the resin layer 5 as illustrated in FIGS. 1D and 1E also allows the excess aqueous polymer solution between the second bonding layer 3 and the curved surface 4 to be efficiently discharged. FIG. 4 is a graph showing the shape of the curved surface 4 of the resin layer 5 and the curved shape of the gold layer 2. The axis of abscissae represents the position, and the axis of ordinates represents the height. In FIG. 4, (a) indicates the shape of the curved surface 4 of the resin layer 5. In FIG. 4, (b) indicates the height of the curved surface 4+120 μm (which corresponds to the total thickness of the first bonding layer 6, the second bonding layer 3, and the gold layer 2). In FIG. 4, (c) indicates the shape of the surface of the gold layer 2 opposite the surface in contact with the second bonding layer 3; i.e. the outer surface of the gold layer. The graph of FIG. 4 shows that the gold layer 2 bonded to the curved surface 4 has a curved shape that reflects the shape of the curved surface 4. The radius of curvature of the contact surface between the gold layer 2 and the second bonding layer 3 is 1197 mm (the radius of curvature of the curved surface 4 of the resin layer 5+120 μm). Thus, the structural body 1 includes the gold layer 2 having a radius of curvature of 1197 mm. The height direction of the holes 7 two-dimensionally arranged in the gold layer 2 is parallel to the direction perpendicular to the curved surface 4.

Figure 1F:
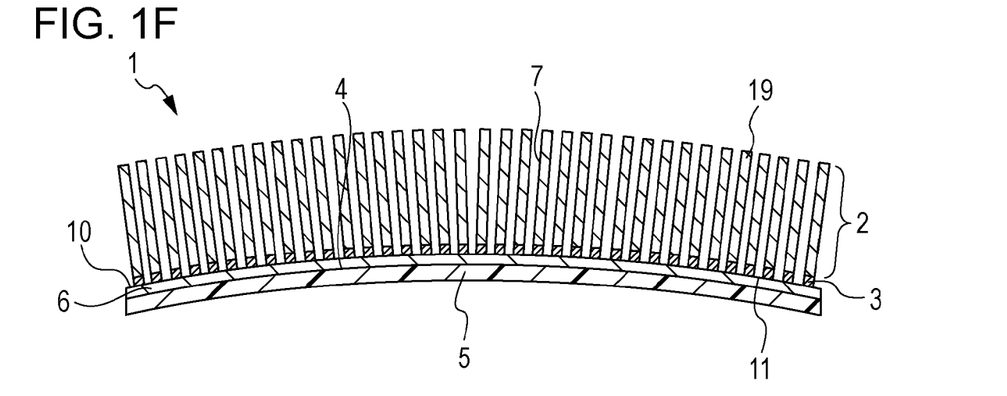

As illustrated in FIG. 1F, the resin layer 5 can have a uniform thickness in a region in which the gold layer 2 is disposed on the curved surface 4 of the resin layer 5. When the structural body 1 that includes the gold layer 2 is used as an X-ray shield grating, the resin layer 5 having a uniform thickness can decrease variations in X-ray transmission through the holes 7 in the gold layer 2 and the resin layer 5. In other words, variations in X-ray transmission resulting from variations in the thickness of the resin layer 5 can be decreased. In this case, the resin layer 5 preferably has a thickness of 3 mm or less, more preferably 1 mm or less. Variations in the thickness of the resin layer 5 are preferably 10% or less, more preferably 3% or less.

Reference Example 1

Figure 5:
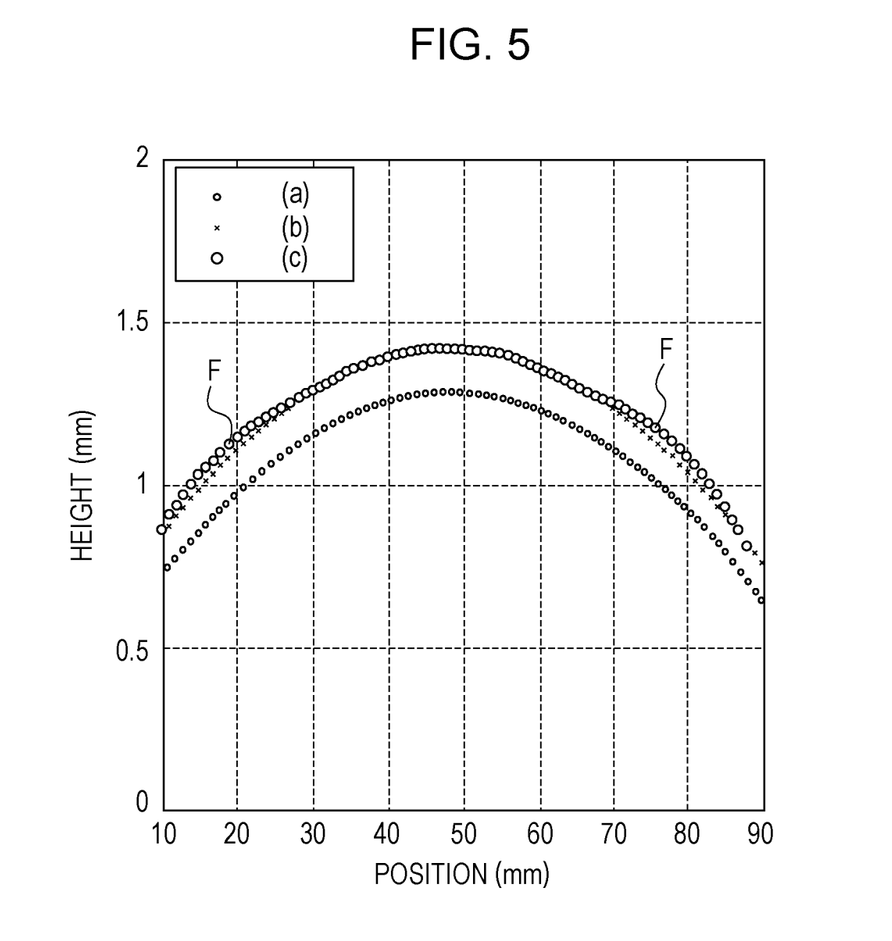
FIG. 5 is a graph for explaining a reference example.

In the present reference example (not covered by the scope of the claims), the gold layer 2, the second bonding layer 3, and the resin layer 5 described in the example of execution 1 are used. In the present reference example, however, the surface (gold surface) of the gold layer 2 opposite the surface in contact with the second bonding layer 3 faces the curved surface 4. Furthermore, instead of bonding the gold layer 2 to the curved surface 4 of the resin layer 5 via the first bonding layer 6 and the second bonding layer 3, only the periphery of the gold layer 2 is bonded to the curved surface 4 of the resin layer 5 with tape. A structural body is formed by bonding the periphery of the gold layer 2 to the curved surface 4 of the resin layer 5 with tape and pressurizing the gold layer 2 using a rubber balloon in the same manner as in the example of execution 1. The total thickness of the tape, the second bonding layer 3, and the gold layer 2 is 120 μm. FIG. 5 is a graph showing the shape of the curved surface 4 of the resin layer 5 and the curved shape of the gold layer 2, wherein (a) indicates the shape of the curved surface 4 of the resin layer 5, (b) indicates the height of the curved surface 4 of the resin layer 5+120 μm, and (c) indicates the shape of the hydrogen-bonding surface of the second bonding layer 3. Comparison of FIG. 4 and FIG. 5 shows that the curved surfaces in the reference example shown in FIG. 5 are less smooth and not symmetrical, implying that the join between the gold layer and the resin contains variations in thickness.

Example of Execution 2

The structural body 1 illustrated in FIG. 1B is described in the present example of execution. The structural body 1 includes the gold layer 2 having a plurality of recess portions 8 arranged in one direction.

Each of the recess portions 8 in the gold layer 2 extends in a line at a width of 4 μm and is disposed at intervals of 8 μm. The recess portions 8 are vertically formed in the gold layer 2 while the gold layer 2 is flat (rather than curved). The gold layer 2 has a thickness of 120 μm, and the linear recess portions 8 have a depth of 115 μm. The resin layer 5 in the present example of execution has a shape of a cylinder having a radius of curvature of 1500 mm cut in a height direction (a semicylindrical shape). The curved surface 4 is a cylindrical surface having a radius of curvature of 1500 mm. A titanium layer and a titanium nitride layer are formed on the gold layer 2 using a vacuum sputtering method. This Ti/TiN layer serves as the second bonding layer 3. In the second bonding layer 3, the titanium nitride surface has a hydrogen-bonding property. The first bonding layer 6 is formed in the same manner as in the example of execution 1. In the present example of execution, the gold layer 2 is bonded to the curved surface 4 of the resin layer 5 probably by the action of hydrogen bonding between hydroxy groups of polyvinyl alcohol and titanium nitride. The gold layer 2 is bent in the direction perpendicular to the longitudinal direction of the linear recess portions 8 and is bonded to the cylindrical surface. Thus, in the resulting structural body, the height direction of the recess portions 8 in the gold layer 2 is perpendicular to the curved surface 4.

Example of Execution 3

The present example of execution is the same as the example of execution 1 except that chromium and $SiO_2$ are disposed in this order as the second bonding layer 3 on the gold layer 2 and the first bonding layer 6 is formed of polyoxyethylene lauryl ether. The $SiO_2$ surface serves as a hydrogen-bonding surface. Also in the present example of execution, like the example of execution 2, the height direction of the recess portions 8 in the gold layer 2 is perpendicular to the curved surface 4 in the resulting structural body.

Example of Execution 4

The structural body 1 illustrated in FIG. 1C is described in the present example of execution. The structural body 1 includes the gold layer 2 having the recess portions 8 arranged in one direction. The recess portions 8 have a lower aspect ratio than the example of execution 2. In the present example of execution, the gold layer 2 has a thickness of 120 μm, and linear protrusions 9 having a width of 4 μm are disposed at intervals of 24 μm. The recess portions 8 are disposed between the linear protrusions 9. As in the example of execution 2, the recess portions 8 are vertically formed in the gold layer 2 in the flat state. Also in the present example of execution, in the resulting structural body, the height direction of the recess portions 8 in the gold layer 2 is perpendicular to the curved surface 4.

Example of Execution 5

An X-ray Talbot interferometer that includes the gold layer 2 of the structural body 1 manufactured in the example of execution 1 as an X-ray shield grating is described in the present example of execution with reference to FIG. 2.

An X-ray Talbot interferometer 1000 includes the X-ray source 100 for emitting a spatially coherent divergent X-ray, a diffractive grating 200 for diffracting the X-ray emitted by the X-ray source 100, a shield grating 300 that includes a shield portion and a transmission portion for the X-ray, and a detector 400 for detecting the X-ray. The diffractive grating 200 diffracts the X-ray emitted by the X-ray source 100 and forms an interference pattern. The shield grating 300 blocks part of the X-ray that forms the interference pattern. The shield grating 300 is the gold layer 2 according to the example of execution 1 and is bonded to the resin layer 5 having the curved surface 4, thus constituting the structural body 1 according to the example of execution 1 (or, indeed any of embodiments 2 to 4). The shield grating 300 is disposed such that the total of the radius of curvature of the curved surface 4 of the resin layer 5 and the thicknesses of the first bonding layer 6 and the second bonding layer 3 is equal to the distance between the X-ray source 100 and a surface of the shield grating 300 facing the X-ray source 100.

Placing the subject 500 between the X-ray source 100 and the diffractive grating 200 forms an interference pattern, which has information on the X-ray phase shift caused by the subject 500. The interference pattern and the shield grating 300 produces a moiré pattern. The intensity distribution of the moiré pattern is detected with the detector 400.

Thus, the X-ray Talbot interferometer 1000 measures (takes images of) the subject 500 by detecting the moiré pattern that has the phase information of the subject 500 with the detector 400. A phase image of the subject 500 can be obtained from the detection results by phase retrieval processing using a Fourier transform method or a phase shift method. The grating region of the shield grating 300 includes the X-ray detection region (detection area) of the detector 400.

While the present invention has been described by way of example with reference to the embodiments above, it is to be understood that the invention is not limited to the disclosed example of executions, but rather to the scope of the following claims.

An X-ray shield grating that can be used for a two-dimensional divergent X-ray can be spherically bent. The present invention can be applied to such an X-ray shield grating.

The technology components described in the present specification or the attached drawings alone or in combination can have technical utility and are not limited to the combinations described in the following claims at the time of filing. The techniques exemplified in the present specification or the attached drawings can simultaneously achieve a plurality of objects and have technical utility by achieving one of the objects.

This application claims the benefit of Japanese Patent Application No. 2013-247127, filed Nov. 29, 2013, which is hereby incorporated by reference herein in its entirety.

The described embodiments can provide a structural body that includes a gold layer that can easily retain a curved shape.

What is claimed is:

1. A structural body, comprising:
   a resin layer with a curved surface;
   a first bonding layer containing a water-soluble polymer;
   a second bonding layer having a hydrogen-bonding surface; and
   a gold layer in this order,
   the first bonding layer being between, and in contact with, the curved surface of the resin layer and the hydrogen-bonding surface of the second bonding layer.

2. The structural body according to claim 1, wherein the gold layer has a plurality of holes.

3. The structural body according to claim 2, wherein the plurality of holes have an aspect ratio of between 7 and 60 inclusive.

4. The structural body according to claim 2, wherein the plurality of holes are disposed at intervals of between 0.5 μm and 10 μm inclusive.

5. The structural body according to claim 2, wherein the plurality of holes are arranged in two dimensions, and the curved surface is a spherical surface.

6. The structural body according to claim 2, wherein the plurality of holes are arranged in one direction, and the curved surface is a cylindrical surface.

7. The structural body according to claim 1, wherein the gold layer has a plurality of recess portions.

8. The structural body according to claim 7, wherein the plurality of recess portions have an aspect ratio of between 7 and 60 inclusive.

9. The structural body according to claim 7, wherein the plurality of recess portions are disposed at intervals of between 0.5 μm and 10 μm inclusive.

10. The structural body according to claim 7, wherein the plurality of recess portions are arranged in two dimensions, and the curved surface is a spherical surface.

11. The structural body according to claim 7, wherein the plurality of recess portions are arranged in one direction, and the curved surface is a cylindrical surface.

12. The structural body according to claim 1, wherein the hydrogen-bonding surface of the second bonding layer is formed of one from a group comprising: a metal oxide, semi-metal oxide, a metal nitride and a semi-metal nitride.

13. The structural body according to claim 1, wherein the curved surface is a spherical surface or a cylindrical surface.

14. The structural body according to claim 1, wherein the first bonding layer contains polyvinyl alcohol.

15. The structural body according to claim 1, wherein the second bonding layer includes a plurality of layers.

16. The structural body according to claim 1, wherein the gold layer has a curved shape.

17. An X-ray Talbot interferometer, comprising:
    a diffractive grating configured to diffract a divergent X-ray emitted by an X-ray source and to form an interference pattern;
    a shield grating configured to block part of the divergent X-ray that forms the interference pattern; and
    a detector configured to detect the divergent X-ray through the shield grating,
    wherein the shield grating includes the structural body according to claim 1.

18. An X-ray Talbot interferometer, comprising:
    a source grating configured to block part of a divergent X-ray emitted by an X-ray source;
    a diffractive grating configured to diffract the divergent X-ray emitted from the source grating and to form an interference pattern; and
    a detector configured to detect the divergent X-ray through the diffractive grating,
    wherein the source grating includes the structural body according to claim 1.

19. The X-ray Talbot interferometer according to claim 18, further comprising a shield grating configured to block part of the divergent X-ray that forms the interference pattern, wherein the shield grating is disposed between the diffractive grating and the detector.

20. A method for manufacturing a structural body, comprising:
    applying an aqueous polymer solution on at least one of a curved surface of a resin layer and a hydrogen-bonding surface of a second bonding layer;
    bringing together the resin layer and the second bonding layer such that the curved surface is in contact with the hydrogen-bonding surface with the aqueous polymer solution interposed therebetween;
    drying the aqueous polymer solution to form a first bonding layer; and
    applying a gold layer to a surface of the second bonding layer opposite the hydrogen-bonding surface.

* * * * *